United States Patent

Kranz

[11] 4,371,700
[45] Feb. 1, 1983

[54] PREPARATION OF 1-AZOLYL-3,3-DIMETHYL-1-PHENOXY-BUTAN-2-OLS

[75] Inventor: Eckart Kranz, Wuppertal, Fed. Rep. of Germany

[73] Assignee: Bayer Aktiengesellschaft, Leverkusen, Fed. Rep. of Germany

[21] Appl. No.: 232,461

[22] Filed: Feb. 9, 1981

[30] Foreign Application Priority Data

Feb. 26, 1980 [DE] Fed. Rep. of Germany ....... 3007079

[51] Int. Cl.³ .................. C07D 249/08; C07D 233/60
[52] U.S. Cl. .................................... 548/262; 548/341
[58] Field of Search ............................ 548/262, 341

[56] References Cited

PUBLICATIONS

Kocian, O., et al., *Coll. Czech. Chem. Comm.*, 44, 1167–1172, (1979).
Kocian, O., et al., *Coll. Czech. Chem. Comm.*, 43, 1413–1430, (1978).
Narita, K., et al., *Chem. Pharm. Bull.*, (Japan), 25, 135–140, (1977).

*Primary Examiner*—Richard A. Schwartz
*Attorney, Agent, or Firm*—Sprung, Horn, Kramer & Woods

[57] ABSTRACT

A process for the preparation of a 1-azolyl-3,3-dimethyl-1-phenoxy-butan-2-ol of the formula

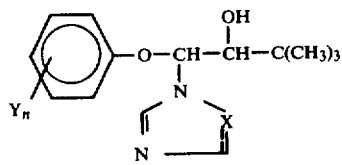

in which
  X is a nitrogen atom or a CH group,
  Y each independently is halogen, phenyl, phenoxy, nitro, alkyl, alkoxy or cycloalkyl, and
  n is 0, 1, 2 or 3,
comprising reacting a 1-azolyl-3,3-dimethyl-1-phenoxy-butan-2-one of the formula

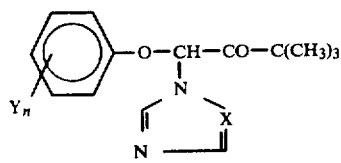

with formic acid/triethylamine in the form of a 5:2 addition compound of the formula

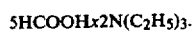

$5HCOOH \times 2N(C_2H_5)_3$.

The product is a known fungicide.

5 Claims, No Drawings

PREPARATION OF 1-AZOLYL-3,3-DIMETHYL-1-PHENOXY-BUTAN-2-OLS

The present invention relates to an unobvious process for the preparation of certain known, fungicidally active 1-azolyl-3,3-dimethyl-1-phenoxy-butan-2-ols.

It has already been disclosed that 1-azolyl-3,3-dimethyl-1-phenoxy-butan-2-ols are obtained when the corresponding keto derivatives are reduced in the customary manner, such as (a) with hydrogen in the presence of a catalyst, for example Raney nickel, and in the presence of a polar solvent, for example methanol, at temperatures from 20° to 50° C., or (b) with aluminum isopropylate in the presence of an inert organic solvent at temperatures from 20° to 120° C., followed by hydrolysis, or (c) with a complex hydride, for example sodium borohydride, in the presence of a polar solvent, for example methanol, at temperatures from 0° to 30° C., followed by hydrolysis, for example with aqueous hydrochloric acid, or (d) with formamidinesulphinic acid and an alkali metal hydroxide, for example sodium hydroxide, in the presence of a polar solvent, for example ethanol, at temperature between 20° and 100° C. (In this context, compare, for example, DE-OS (German Published Specification) No. 2,324,010 [LeA 14 971] and DE-OS (German Published Specification) No. 2,333,354 [LeA 15 148]). The processes mentioned are in some cases troublesome and expensive to carry out.

It has also been disclosed that formic acid/triethylamine in the form of a 5:2 addition compound can be employed for reduction reactions on C-C and C-N double bonds, for example for the reduction of $\alpha,\beta$-unsaturated ketones, the carbonyl groups themselves not being attacked (see inter alia, Chem. Pharm. Bull. 17, 747 (1969) and 18, 1530 (1970)).

The present invention now provides a process for the preparation of a 1-azolyl-3,3-dimethyl-1-phenoxy-butan-2-ol of the general formula

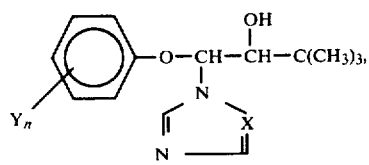

(I)

in which
X represents a nitrogen atom or the CH group,
Y represents halogen, phenyl, phenoxy, nitro, alkyl, alkoxy, or cycloalkyl and
n represents 0, 1, 2 or 3, each Y being selected independently when n is 2 or 3,
in which a 1-azolyl-3,3-dimethyl-1-phenoxy-butan-2-one of the general formula

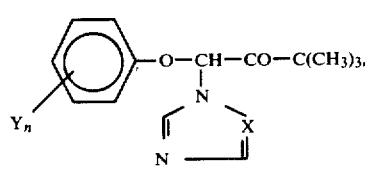

(II)

in which

X, Y and n have the abovementioned meanings, is heated with formic acid/triethylamine in the form of a 5:2 addition compound of the formula $$5HCOOH \times 2N(C_2H_5)_3 \qquad (III).$$

It is surprising that the end products are obtained in a relatively good yield by the process according to the invention, since, on the basis of the state of the art, it was not to be expected that the carbonyl groups can be reduced with the reagent according to the invention.

The process according to the invention has the advantage that a new reducing agent for carbonyl groups which is easy to handle and inexpensive is provided by the formic acid/triethylamine 5:2 addition product.

Formula (I) provides a general definition of the 1-azolyl-3,3-dimethyl-1-phenoxy-butan-2-ols which can be prepared by the process according to the invention. Preferably, in this formula, Y represents fluorine, chlorine, bromine, iodine, phenyl, phenoxy, nitro, straight-chain or branched alkyl or alkoxy with in either case 1 to 4 carbon atoms or cycloalkyl with 5 or 6 carbon atoms.

If, for example, 1-(4-chlorophenoxy)-3,3-dimethyl-1-(1,2,4-triazol-1-yl)-butan-2-one is used as the starting material, the course of the reaction can be represented by the following equation:

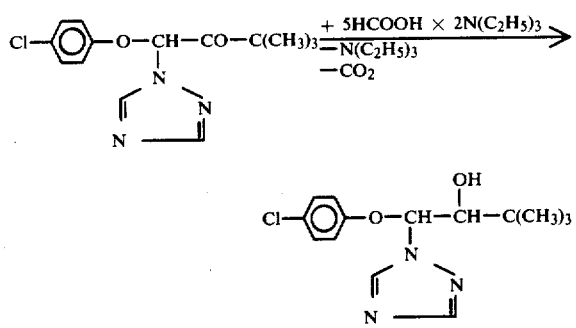

The 1-azolyl-3,3-dimethyl-1-phenoxy-butan-2-ones of the formula (II) are known (see DE-OS (German Published Specification) No. 2,105,490 [LeA 13 458] and DE-OS (German Published Specification) No. 2,201,063 [LeA 14 118]).

The reaction according to the invention is carried out in the absence of solvents.

The reaction temperatures can be varied within a substantial range in carrying out the process according to the invention. In general, the reaction is carried out between about 80° and 200° C., preferably between about 100° and 160° C.

In carrying out the process according to the invention, about 1 to 4 mols of reducing agent of the formula (III) are employed per mol of ketone of the formula (II). The end products are isolated in the generally customary manner.

As is known, the substances which can be prepared according to the invention are distinguished by a very good fungicidal activity (see German Offenlegungsschriften (German Published Specification) No. 2,324,010 [LeA 14 971] and No. 2,333,354 [LeA 15 148]).

Fungicidal agents in plant protection are employed for combating Plasmodiophoromycetes, Comycetes, Chyrtridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methyl-cellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, bactericides, insecticides, acaricides, nematicides, herbicides, bird repellents, growth factors, plant nutrients and agent for improving soil structure.

The active compounds can be used as such, as their formulations or as the use forms prepared therefrom by further dilution, such as ready-to-use solutions, emulsions, suspensions, powders pastes, and granules. They may be used in the customary manner, for example by watering, immersion, spraying, atomizing, misting, vaporizing, injecting, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of in general 0.001 to 50 g, preferably 0.01 to 10 g, are employed per kilogram of seed.

For the treatment of soil, active compound concentrations of in general 0.00001 to 0.1% by weight, preferably 0.0001 to 0.02%, are employed at the place of action.

The present invention also provides a fungicidal composition containing as active ingredient a compound prepared by the process of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound prepared by the process of the present invention alone or in the form of a composition containing as active ingredient such a compound in admixture with a diluent or carrier.

The present invention further provides crops protected from damage by fungi by being grown in areas in which immediately prior to and/or during the time of the growing a compound prepared by the process of the present invention was applied alone or in admixture with a diluent or carrier.

The process according to the invention is illustrated by the following preparative examples:

PREPARATION EXAMPLES

Example 1

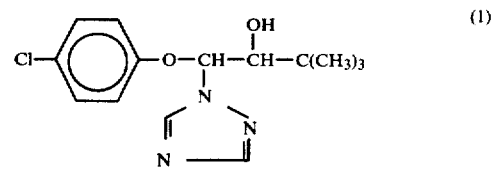

28.45 g (0.1 mol) of 1-(4-chlorophenoxy)-3,3-dimethyl-1-(1,2,4-triazol-1-yl)-butan-2-one and 43.25 g (0.1 mol) of formic acid/triethylamine (5:2 addition compound) were heated to 145° to 150° C. for 4.5 to 5 hours. The reaction mixture was allowed to cool and was concentrated in vacuo. The residue was taken up in dilute sodium hydroxide solution and the mixture was extracted with methylene chloride. The organic phase was washed with water, dried over sodium sulphate and concentrated in vacuo. The residue was suspended in hot cyclohexane, the suspension was filtered hot and the solid was dried. 18.2 g (63.6% of theory) of 1-(4-chlorophenoxy)-3,3-dimethyl-1-(1,2,4-triazol-1-yl)-butan-2-ol of melting point 114°-116° C. were obtained.

EXAMPLE 2

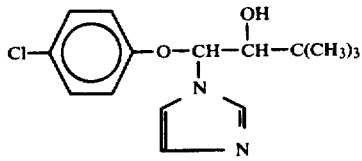 (2)

14 g (0.048 mol) of 1-(4-chlorophenoxy)-3,3-dimethyl-1-(imidazol-1-yl)-butan-2-one and 61.8 g (0.143 mol) of formic acid/triethylamine (5:2 addition compound) were heated at 145° C. for 4 hours. The reaction mixture was allowed to cool and was concentrated in vacuo. The residue was taken up in dilute sodium hydroxide solution and the mixture was extracted with methylene chloride. The organic phase was washed with water, dried over sodium sulphate and concentrated in vacuo. The residue was suspended in hot cyclohexane, the suspension was filtered hot and the solid was dried. 7.9 g (56% of theory) of 1-(4-chlorophenoxy)-3,3-dimethyl-1-(imidazol-1-yl)-butan-2-ol of melting point 145°-147° C. were obtained.

The following compounds of the general formula

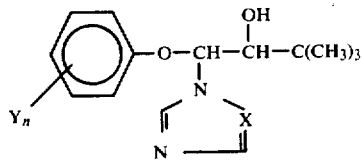 (I)

could be prepared in an analogous manner:

| Compound No. | $Y_n$ | X | Melting point (°C.) |
|---|---|---|---|
| 3 | 4-NO$_2$ | N | 194–96 |
| 4 | 2,4-Cl$_2$ | N | 114–16 |
| 5 | 4-C(CH$_3$)$_3$ | N | 113–17 |
| 6 | 4-Br | N | 115–18 |
| 7 | 2,4,5-Cl$_3$ | N | 137–44 |
| 8 | 4-CH$_3$ | N | 123–27 |
| 9 | 2-Cl | N | 107–12 |
| 10 | 3,4-(CH$_3$)$_2$ | N | 133–35 |
| 11 | 2-CH$_3$,4-Cl | N | 107–10 |
| 12 | 3-Cl | N | 114–15 |
| 13 | 4-F | N | 99–110 |
| 14 | — | N | 88–94 |
| 15 | 4—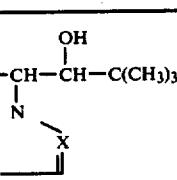 | N | 98–109 |
| 16 | 4—(H) | N | 115–20 |
| 17 | 2-Cl, 4—◯ | N | 95–98 |
| 18 | 2,6-Cl$_2$, 4—◯ | N | 142–44 |
| 19 | 2,6-Cl$_2$ | CH | 95–102 |
| 20 | 2,4 Cl$_2$ | CH | 101–09 |
| 21 | 4-F | CH | 103–05 |
| 22 | 3-Cl | CH | 102–06 |
| 23 | — | CH | 99–105 |
| 24 | 4—◯ | CH | 136–40 |
| 25 | 4-C(CH$_3$)$_3$ | CH | 145–50 |
| 26 | 4-Br | CH | 173–74 |
| 27 | 4—(H) | CH | 134–40 |
| 28 | 2-Cl, 4—◯ | CH | 86–95 |
| 29 | 2,6-Cl$_2$, 4—◯ | CH | 110–13 |
| 30 | 4-I | CH | 192–94 |
| 31 | 2-F | CH | 118–30 |
| 32 | 3-Br | CH | 125–27 |
| 33 | 3-CH$_3$ | CH | 92–94 |

It will be appreciated that the instant specification and examples are set forth by way of illustration and not limitation, and that various modifications and changes may be made without departing from the spirit and scope of the present invention.

I claim:

1. A process for the preparation of a 1-azolyl-3,3-dimethyl-1-phenoxy-butan-2-ol of the formula

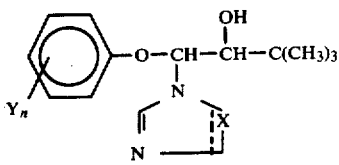

in which

X is a nitrogen atom or a CH group,

Y each independently is halogen, phenyl, phenoxy, nitro, alkyl, alkoxy or cycloalkyl, and n is 0, 1, 2 or 3, comprising reacting a 1-azolyl-3,3-dimethyl-1-phenoxybutan-2-one of the formula

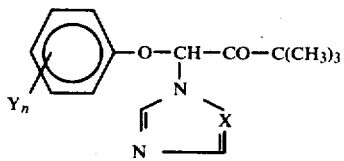

with formic acid/triethylamine in the form of a 5:2 addition compound of the formula 5HCOOHx2N(C₂H₅)₃, about 1 to 4 mols of the addition compound being employed per mol of 1-azolyl-3,3-dimethyl-1-phenoxybutan-2-one.

2. A process according to claim 1, wherein the reaction is carried out at a temperature from about 80° to 200° C.

3. A process according to claim 1, wherein the reaction is effected in the absence of a solvent.

4. A process according to claim 1, in which Y is fluorine, chlorine, bromine, iodine, phenyl, phenoxy, nitro, alkyl or alkoxy with 1 to 4 carbon atoms, or cycloalkyl with 5 or 6 carbon atoms.

5. A process according to claim 4, wherein the reaction is effected in the absence of a solvent at a temperature from about 100° to 160° C.

* * * * *